United States Patent [19]
Leight

[11] Patent Number: 5,824,966
[45] Date of Patent: Oct. 20, 1998

[54] ENHANCED BAND EARPLUG

[75] Inventor: Howard S. Leight, San Diego, Calif.

[73] Assignee: Bacou USA Safety, Inc., Del.

[21] Appl. No.: 955,919

[22] Filed: Oct. 22, 1997

[51] Int. Cl.⁶ .................................................. H04R 25/02
[52] U.S. Cl. .......................................... 181/130; 181/135
[58] Field of Search ................................... 181/129, 130, 181/131, 135, 137; 381/183, 187; 128/857, 864–868

[56]  References Cited

U.S. PATENT DOCUMENTS

| | | | |
|---|---|---|---|
| 2,498,960 | 2/1950 | Mullin | 181/131 |
| 2,780,681 | 2/1957 | Shaper | 181/131 |
| 3,667,569 | 6/1972 | Mackey et al. | 181/135 |
| 4,819,624 | 4/1989 | Leight et al. | 128/866 |
| 5,298,691 | 3/1994 | Leight | 181/135 |

*Primary Examiner*—Khana Dang
*Attorney, Agent, or Firm*—Freilich Hornbaker and Rosen

[57] ABSTRACT

A noise blocking band earplug has a band (12) with outer portions (44, 46) that are bent to prevent the ear-engaging pods (20, 22) from touching the ground, whether placed right-side-up or upside-down on the ground. When the middle region (32) of the band rests on a horizontal surface (64), a band inner end part (70) extends at an upward incline (C) with its outer end forming a second bend (80) so the outer end part (72) extends at a downward incline (D), with the second bend preventing the pods from touching the ground when the earplug is laid upside-down. At the second bend (80), the largely vertical height (J) of the band is increased and its outer surface (102) is made convex to provide pods for more readily pressing the pods against the outside of the ear canals.

8 Claims, 2 Drawing Sheets

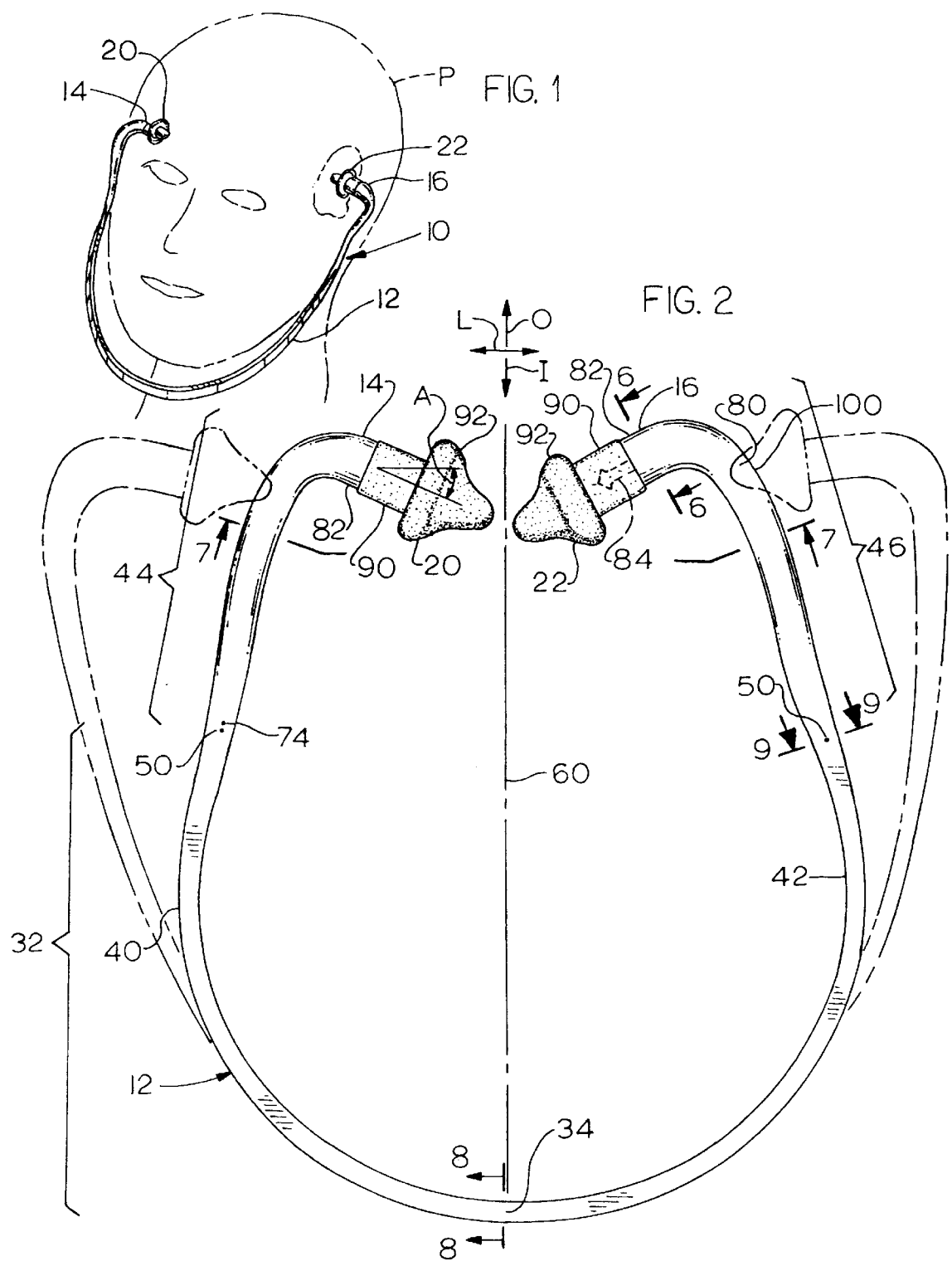

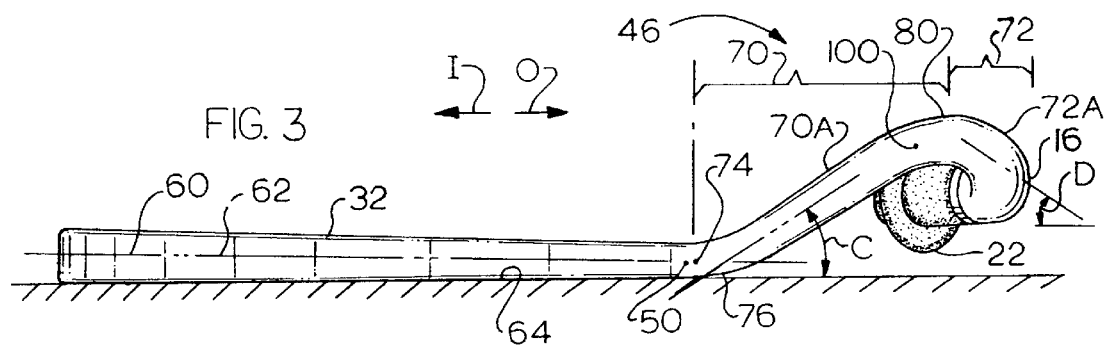
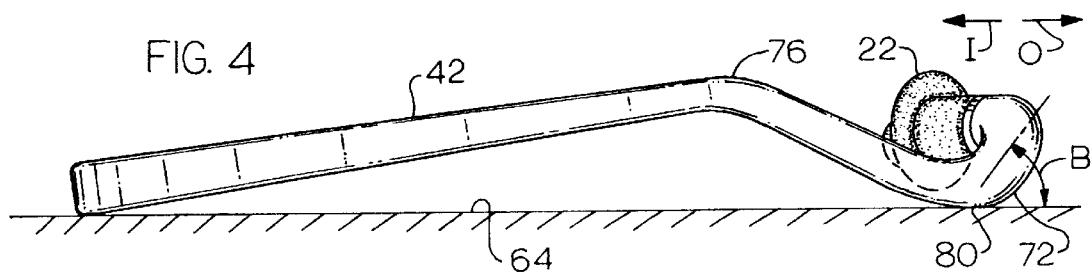
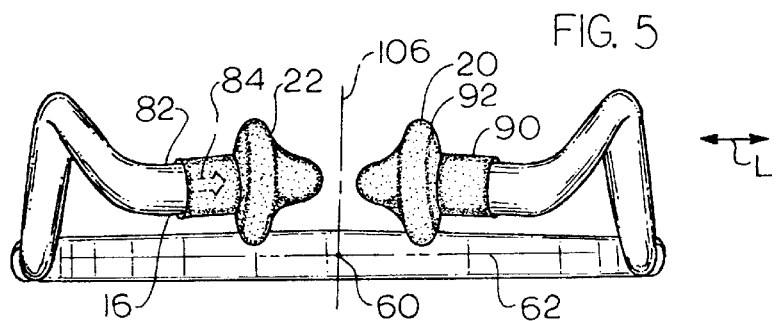
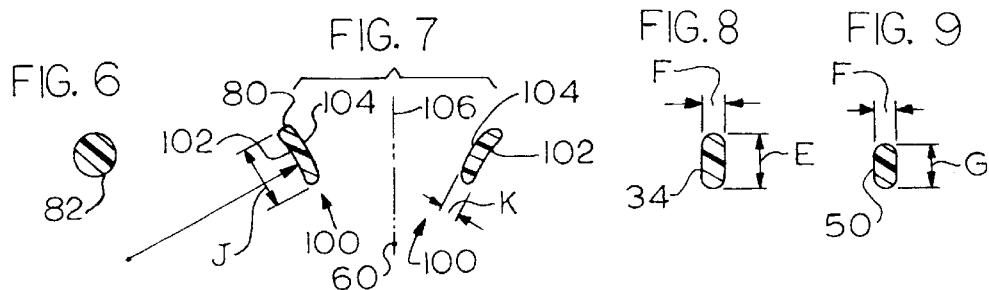

ENHANCED BAND EARPLUG

BACKGROUND OF THE INVENTION

My earlier U.S. Pat. No. 5,298,691 entitled "SOILING RESISTANT BANDED EARPLUG" describes a band earplug that avoids soiling of the earplug devices, or pods that actually press against the outside of a person's ear canals. The patent describes the band outer portions as angled to extend at an upward-outward incline when the middle portion of the band rests on a horizontal surface. If a worker places the band right-side-up even on a dirty surface, the band holds the pods away from the surface so they will not be soiled. Such soiling of the pads could lead to dirtying the worker's ears, or require a new clean band earplug.

Workers often lay a band earplug on a dirty surface without taking care to make sure that the band is laid right-side-up to protect the pods from dirt. It would be desirable if a band earplug were constructed to avoid soiling of the pods, no matter what orientation the band earplug was laid onto a dirty surface.

SUMMARY OF THE INVENTION

In accordance with one embodiment of the present invention, a band earplug is provided, which avoids soiling when laid right-side-up or upside-down on a largely horizontal dirty surface. The band earplug includes a band of largely U-shape with a middle region and with opposite end portions, and with pods mounted on each band outer end. Each outer end portion has parts that are angled to extend at upward and downward inclines from the horizontal when the middle portion extends horizontally. As a result, when the band earplug is laid right-side-up or upside-down on a horizontal surface, the ends of the inclined portions will prevent the pods from touching the surface.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of a band earplug of the present invention, shown how it is worn by a wearer.

FIG. 2 is a plan view of the band earplug of FIG. 1, when the middle portion lies in a horizontal plane.

FIG. 3 is a side elevation view of the band earplug, shown lying right-side-up on a horizontal surface.

FIG. 4 is a view similar to that of FIG. 3, but with the band earplug oriented upside-down while lying on the horizontal surface.

FIG. 5 is a front elevation view of the earplug of FIG. 2.

FIG. 6 is a sectional view taken on line 6—6 of FIG. 2.

FIG. 7 is a sectional view taken on the line 7—7 of FIG. 2.

FIG. 8 is a view taken on line 8—8 of FIG. 2.

FIG. 9 is a view taken on line 9—9 of FIG. 2.

DESCRIPTION OF THE PREFERRED EMBODIMENT

FIG. 1 illustrates a band earplug 10 which includes a resilient band 12 designed to extend about halfway around the head of a person P, and which has opposite outer ends 14, 16. A pair of pods 20, 22 are each attached to a different one of the band outer ends. The resilient band 12 urges the pods towards the person's ears, so each pod presses against the entrance to a person's ear canal to form a seal therewith which minimizes the passage of noise to the person's inner ear.

Band earplugs of this general type are well known, and are commonly used in work places such as factories, where they are reused many times before disposal. Workers commonly remove the earplugs for extended periods such as during coffee and lunch breaks, when the band earplugs must be stored. Such storage is commonly achieved by merely laying the band earplug on an easily available surface such as an unused region of a table, which may be referred to as a ground surface. Since surfaces in manufacturing plants often become dirty from oil, bits of metal that have been ground or machined from work pieces, and other soiling material, the pods often become soiled. If a workman places a soiled pod against one of his ears, the soiling material may harm the worker, or at least feel uncomfortable. An alternative is for the worker to request another banded earplug, which results in additional expense.

In my earlier U.S. Pat. No. 5,298,691, I describe a band earplug which can be laid on a surface but which holds the pod away from the surface to avoid soiling it. However, that band earplug requires that the band be laid in a right-side-up orientation on the surface. Workers often do not pay attention as to which side is down, and may lay the band earplug upside-down, causing the pod to become soiled. Also, band earplugs sometimes fall from the worker onto a bench, and initially reach the bench surface in an uncontrolled orientation.

In accordance with the present invention, the band earplug 10 is constructed so that when laid in almost any orientation on a largely flat and horizontal surface, as in the right-side-up orientation of FIG. 3 and the upside-down orientation of FIG. 4, the pods such as 22 will not touch that surface and become soiled. Also, if the band earplug is placed so it leans against an object while its outer end 14, 16 lies against a soiled surface, or the band earplug drops so its outer end 14, 16 encounters a soiled surface, the pods generally will not be soiled.

The band 12 of FIG. 2 has a middle region 32 with a middle 34 and opposite middle portions 40, 42 on opposite sides of the middle. The earplug also has a pair of opposite end portions 44, 46 with outer pod-holding ends 14, 16 at the outer ends of the band. Each end portion 44, 46 merges with a middle portion at a mid-end, or far location 50 which is the outermost part (in direction O) of the corresponding middle portion. The band is substantially symmetrical about an imaginary horizontal centerline 60 that passes through the middle 34 and halfway between the outer ends 14, 16. As shown in FIG. 3, the band has a horizontal center plane 62 that extends through the horizontal center line 60 and that extends substantially horizontal (within 10° and preferably 5° of horizontal) when the earplug lies in its right-side-up position shown in FIG. 3 and lies on a horizontal surface 64.

Each of the outer end portions such as 46 has inner and outer end parts 70, 72 that are positioned with respect to the inward and outward arrows I, O. The inner end part 70 is closest to the middle portion 42 and is joined to a far location 50 at the inner end 74 of the inner end part 70. The locations 50, 74 are joined near a first bend 76 whose lower surface is convex and whose upper surface is concave. The bend 76 results in most 70A of the inner end part 70 extending at an upward-outward incline at an angle C of about 30°. The inner and outer end parts 70, 72 are joined at a second bend 80 of about 70° whose upper surface is convex and whose lower surface is concave in FIG. 3. Most 72A of the outer end part 72 extends at a downward-outward incline at an average angle D of about 30° as seen in the side view at FIG. 3. The outer end such as 16, shown in FIGS. 2 and 5, includes an outer shaft section 82 with a post 84 at its end, which is fixed to the corresponding pod 20, 22. Each pod includes a cylindrical section 90 with a hole that receives the post, and a flange section 92 that actually engages the wearer's ear. Both are preferably of foam plastic.

As shown in FIG. 3, the middle region 32 extends along most of the length of the band and generally has the greatest weight, so the band earplug rests with the band middle region 32 lying almost "flat" against the horizontal surface. The first bend 76 results in the outer end portion 46 extending generally at an upward-outward incline to keep the pod 22 raised above the horizontal surface 64. In the event that the band is laid upside-down on the horizontal surface 64, as shown in FIG. 4, the second bend 80 prevents the pod 22 from touching the surface. The second bend 80 results in the outer part 72 extending at an upward-outward incline B in the upside-down position of the band earplug so the pod 22 is again held above the surface 64 and is not soiled even when the earplug is laid upside-down on a horizontal surface.

FIG. 2 shows that the outer shaft sections 82 extend at angles A to the lateral direction L so the shaft sections 82 extend inwardly (I) and towards the opposite side of the earplug, to position the pods 20, 22 so even if the band is laid on a surface so the band outer ends 14, 16 are supported on the surface, the pads 22 will not touch that surface.

The outer end portion 46 of the band has a region 100 of increased largely vertical height at the bend 80. As shown in FIG. 7, each region 100 has largely flattened and slightly convex laterally distal surface 102 and a convex laterally proximal surface 104. The surface 102 is angled about 45° from the horizontal, which is accomplished by "twisting" the band along each end portion. The terms distal and proximal are relative to a vertical center plane 106 that extends through the middle of the band. The distal surfaces 102 provide pads where the wearer's fingers can rest to press the pods against the outsides of his ear canals. It is noted that applicant prefers to form the pod flange sections 92 of slow recovery foam material. While the band presses the pods towards each other with a force of about seven ounces, it requires a few more ounces to seat the pods against the outside of the ear canal so they seal well thereat. The wide finger-pressed pad surfaces 102 enhance this.

For the band earplug illustrated, FIG. 8 shows that at the middle 34 the band has a height E of 9.3 mm and a width F of 3.8 mm. At the far locations 50, FIG. 9 shows that the height G is 7.3 mm and the width F is still about 3.8 mm. The average height along the middle region is about 8.3 mm. FIG. 7 shows that at the bend 80, the band has a largely (but inclined) height J of 10.5 mm and a width K of 3.4 mm. FIG. 6 shows that along the shaft 82 of FIG. 2, the shaft is largely circular, with a diameter of about 9.8 mm.

Thus, the invention provides a band earplug that resists soiling of the pods when the band is laid on a horizontal surface, either right-side-up or upside-down. This is accomplished by providing two bends in the outer portions of the band to form two inclined end parts, with the inner end part extending at an incline in one direction and the outer end part extending at an incline in the opposite direction, to provide bends where the band holds the pods above the ground surface. At the outermost one of the two bends, the band has an increased largely vertical height which is preferably flat or concave, to serve as pressing surfaces or pads where a person can press against the earplugs to seat them against the outer surfaces of his ear canals.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A band earplug apparatus, comprising:

a band (12) constructed to extend about halfway around a person's head, said band having a middle region (32) with a middle (34) and with opposite mid-ends forming far points (50), and said band having opposite end portions (44, 46) with outer pod-holding ends (14, 16) that can lie opposite the ears of the person and inner ends (74) that merge with said far points;

a pair of pods (20, 22) each mounted on one of said band outer pod-holding ends and constructed to seal against the outside of the person's ear canal, with said band urging its outer pod-holding ends together to urge said pods against the outside of the person's ear canals;

said band being substantially symmetrical about an imaginary substantially horizontal centerline (60) that passes through said middle and halfway between said outer ends, and said band having a substantially horizontal centerplane (62) that extends through said middle and said far points;

each of said end portions having inner and outer end parts (70, 72) lying respectively closest and furthest from said middle region, with each of said inner end parts (70) joined to one of said middle portion far points at a first downwardly-convex bend (76) that results, when said centerplane is horizontal and said band is in a right-side-up orientation, in said inner part extending at an upward-outward incline (C) to said centerplane as seen in a horizontal side view that is perpendicular to said centerline, and with each outer end part joined to the corresponding inner end part at a second upwardly-convex bend (80) that results in said outer end part (72) extending at a downward-outward incline (D) to said centerplane, to hold said pods away from a horizontal surface on which it is laid in either said right-side-up orientation or an upside-down orientation.

2. The apparatus described in claim 1 wherein:

said band has a largely horizontal thickness (F) and a largely vertical height (G) along said middle portion at said far end, with said height being greater than said thickness;

at said second upwardly-convex bend (80), each of said band outer end portions (44, 46) has an increased height (J) which is greater than the height at said far points.

3. The apparatus described in claim 2 wherein:

at each of said upwardly-convex bends (80) said band has an outside surface (102) which is twisted from an orientation parallel to the band at the corresponding far location, so each outside surface faces at a downward incline when said centerplane is horizontal.

4. The apparatus described in claim 3 wherein:

each of said outside surfaces is concave along most of its height.

5. The apparatus described in claim 1 wherein:

each of said pods includes a wide ear-engaging part (92) and a mount part (90);

each of said outer pod-holding ends comprises an outer shaft section (82) with a post (84) that holds one of said pod mount parts, with said outer shaft section extending primarily horizontally and toward the other shaft section, but at an inward angle (A) toward said middle of said band middle region which is sufficient to space said ear-engaging part a plurality of millimeters inward of the outermost part of said outer shaft section.

6. A noise blocking band earplug comprising:

a band (12) extending in largely a U-shape, with a middle region (32) and with largely parallel opposite end portions (44, 46);

a pair of pods (20, 22) each mounted on one of said outer end portions and constructed to seal against the outside of a person's ear canal, with said band urging said pods toward each other;

said opposite end portions have inner and outer end parts (70, 72) that are angled to extend, when said middle region extends horizontally, so one of said end parts extends at an upward-outer incline (C) and the other one of said end parts extends at a downward-outer incline (D), with each of said opposite end portions having an outer shaft section (82) that supports one of said pods, so when said band earplug is laid right-side-up or upside-down on a flat horizontal surface no part of said pods touch the horizontal surface.

7. The apparatus described in claim 6 wherein:

said middle region lies in a predetermined substantially horizontal plane (62) and has far ends (50) that merge with said end portions, said middle region has a predetermined average height and said outer end portions each have press pads of a height (J) greater than said middle portion average height.

8. The apparatus described in claim 6 wherein:

each of said end portions has an inner part (70A) extending at an upward-outward incline and an outer part (72A) extending at a downward-outward incline, and with said inner and outer parts joined at an upward-convex second bend (80) where the upper surface at the bend is convex, when said band is right side-up and lies on a horizontal surface;

said outer part (72A) extends at an upward-outward incline and said band rests on said second bend (80) and on said middle region, when said band is upside-down and rests on said horizontal surface.

\* \* \* \* \*